United States Patent [19]

Diekhaus et al.

[11] Patent Number: 4,943,663

[45] Date of Patent: Jul. 24, 1990

[54] PROCESS FOR THE PREPARATION OF α-ALKYLACROLEINS

[75] Inventors: Gerhard Diekhaus; Harald Kappesser, both of Oberhausen, Fed. Rep. of Germany

[73] Assignee: Hoechst Aktiengesellschaft, Fed. Rep. of Germany

[21] Appl. No.: 274,829

[22] Filed: Nov. 22, 1988

[30] Foreign Application Priority Data

Nov. 27, 1987 [DE] Fed. Rep. of Germany ....... 3740293

[51] Int. Cl.$^5$ .............................................. C07C 45/00
[52] U.S. Cl. ..................................... 568/461; 568/463
[58] Field of Search ................................ 568/461, 463

[56] References Cited

U.S. PATENT DOCUMENTS 4,346,239  8/1982  Bach et al. ........................... 568/461
4,408,079  10/1983  Merger ................................. 568/461

FOREIGN PATENT DOCUMENTS 0058927  9/1982  European Pat. Off. ............ 568/461
0092097  10/1983  European Pat. Off. ............ 568/461
2444659  7/1980  France .
2037767  7/1980  United Kingdom ................ 568/461
2078748  1/1982  United Kingdom ................ 568/461

*Primary Examiner*—Werren B. Lone
*Attorney, Agent, or Firm*—Jordan B. Bierman

[57] ABSTRACT

A process for the preparation of alpha-alkylacroleins from aldehydes and formaldehyde. The reaction takes place in the presence of a secondary amine and a carboxylic acid having up to 5 carbon atoms, and is performed in two stages so that, in the first stage, part of the carboxylic acid is added to the reaction mixture and, in the second stage, the remaining carboxylic acid is added.

19 Claims, No Drawings

PROCESS FOR THE PREPARATION OF α-ALKYLACROLEINS

The present invention relates to an improved process for the preparation of alpha-alkylacroleins by the reaction of aldehydes having the general formula

with formaldehyde.

Numerous processes for the preparation of methacrolein are known. Of these processes, the ones which proceed from propionaldehyde have gained in significance in recent years as the starting materials are readily accessible. For example, a yield of approximately 46% of methacrolein is obtained by condensation of the starting aldehydes on catalysts containing sodium hydroxide and silicic acid (cf. C.A. volume 56 [1962], columns 2321 and 2322).

The DE-C1 875 194 describes the preparation of methacrolein by the addition of piperidine dropwise to a mixture of aqueous formaldehyde solution, propionaldehyde, sodium chloride, and butyric acid at boiling temperature over a period of 2 to 3 hours. After another 3 hours after-reaction, a 95% yield of methacrolein is supposed to be obtained. Apart from the fact that long reaction times are necessary, it was not possible to obtain anything near high yield when the instructions were followed.

According to the teachings of DE-B2 28 55 504, propionaldehyde is reacted with formaldehyde to prepare methacrolein. The reaction takes place in a catalyst system consisting of a secondary amine and a carboxylic acid having up to 5 carbon atoms. The reactants are reacted at temperatures of 70° to 120° C. and pressures of 2 to 10 bar. The process gives 80 to 82% yields of methacrolein. DE-A1-30 25 350 describes a general broadening of the above-described process to cover the preparation of 2-methylene aldehydes.

The subject of DE-A1 31 06 557 is a process for the preparation of alpha-alkylacroleins by the reaction of alkanals with formaldehyde and secondary amine in the presence of acid. The reaction takes place in an acidic to neutral environment at pH values of 2.5 to 7. According to the examples, high yields of methacrolein of 90% and more are obtained, but the process requires extremely large amounts of amine; e.g. 0.5 to 1 equivalent per mole of alkanal.

DE-A1 32 13 681 also relates to a process for the preparation of alpha-alkylacroleins from alkanals and formaldehyde in the presence of secondary amines and, optionally, of acids. The reaction is conducted under pressure, at a temperature of more than 150° C., and with a maximum reaction time of 25 minutes. This process also provides methacrolein in high yields, but requires the employment of comparatively high temperatures and pressures.

Therefore, the problem was to develop a procedure which would produce alpha-alkylacroleins in high yields under as mild reaction conditions as possible.

The solution is a process for the preparation of alpha-alkylacroleins from formaldehyde and starting aldehydes with the general formula

R being a straight or branched chain alkyl group having 1 to 10 carbon atoms. There are also present, per mol of aldehyde, 0.02 to 0.05 moles of a secondary amine, and 0.02 to 0.065 moles of a carboxylic acid having up to 5 carbon atoms. The reaction is carried out at 70° to 120° C. under a pressure of 0.2 to 1 MPa. The process provides that the molar ratio of amine to carboxylic acid is 1:0.8 to 1:1.3 and the reaction is performed in two stages: (1) the starting aldehyde and formaldehyde being reacted in the presence of the secondary amine and 25 to 75 mole % of the total carboxylic acid and (2) the reaction being completed after the remaining carboxylic acid has been added. Surprisingly, the foregoing measures lead to high yields of alpha-alkylacroleins in a short time, even though the reaction is carried out at moderate temperatures and only slightly elevated pressure.

R in the general formula of the aldehydes used as starting materials is an alkyl group with 1 to 10 carbon atoms. This group can be straight or branched chain. Examples of suitable aldehydes are propanal, n-butanal, 3-methylbutanal, n-pentanal, n-hexanal, 3-methylhexanal, 4-methylhexanal, and n-heptanal. The process has proven particularly successful when reacting propanal, n-butanal, or 3-methylbutanal.

Formaldehyde is generally employed as an aqueous solution. However, it can also be used in a polymerized form, such as paraformaldehyde. The starting aldehyde and formaldehyde can be reacted in the stoichiometric ratio. However, it is also possible to use one of the two aldehydes in excess. It has proved useful to use 0.9 to 1.5 moles of formaldehyde per mole of starting aldehyde. The use of a solvent, apart from water, in which the formaldehyde can be dissolved is not necessary but is expedient, especially when a polymeric form of the formaldehyde is used. Suitable solvents are hydrocarbons and aliphatic alcohols; e.g. isodecane, toluene, and 2-ethylhexanol.

An important feature of the claimed process is the use of secondary amines and carboxylic acids, both acting together as catalysts, in certain ratios to each other and to the aldehydes; i.e. 0.02 to 0.05, preferably 0.025 to 0.035, mols of a secondary amine and 0.02 to 0.065, preferably 0.025 to 0.040, mols of a carboxylic acid with up to 5 carbon atoms, are used per mol of aldehyde. Furthermore, it is a characteristic of the new process that the molar ratio of amine to carboxylic acid is 1:0.8 to 1.3. Amine and carboxylic acid are preferably added in a molar ratio of 1:1 and, most preferably, in a molar ratio of about 1:1.1 to 1.3.

Both lower and higher molecular weight aliphatic compounds can be used as the secondary amines. The alkyl groups can be the same or different. Examples of suitable secondary amines are dipropylamine, methylbutylamine, ethylbutylamine or di-n-octylamine. Di-n-butylamine has proven particularly successful. The secondary amines do not have to be used as a homogeneous substances, mixtures of the isomers of the same amine or mixtures of different amines have proved well suited for the performance of the reaction.

The carboxylic acids with up to 5 carbon atoms can contain one or more carboxyl groups. Formic acid, acetic acid and, in particular, propionic acid, butyric acid or valeric acid have proven useful. Mixtures of such acids are also satisfactory.

Another very important feature of the procedure according to the invention is the performance of the reaction in two stages. The starting aldehyde and formaldehyde are first reacted with some of the carboxylic acid in the presence of all the secondary amine. The remaining carboxylic acid is then added. In the first stage, 25 to 75, preferably 30 to 65, mol % of the carboxylic acid is added to the reaction mixture, the rest is added in the second stage. It is expedient to perform both stages of the reaction in the same reactor. It was not to be foreseen that the portionwise addition of acid, which means that the reaction takes place in different pH ranges, would lead to an appreciable increase in yield.

Normally, the reaction takes place in the liquid phase with the reaction pressure being maintained between 0.2 and 1 MPa, preferably 0.2 to 0.4 MPa. However, it is also possible to perform the reaction in the gaseous phase. The reaction temperature is between 70° and 120° C., and temperatures of 95° to 110° C. are preferred.

When the reaction takes place in the liquid phase, a pressure vessel is employed in which the aldehyde and formaldehyde are placed under a nitrogen atmosphere with, optionally, the amount of the carboxylic acid to be used in the first stage. It is expedient to then add the secondary amine with intensive stirring. It is also possible to add the amine and carboxylic acid to the original aldehyde mixture. If necessary, the reaction mixture is cooled to maintain it within the reaction temperature range. However, by adding the reactants in portions, it can be ensured that the reaction temperature is not exceeded.

After all the amine has been added, the mixture is left to react for 20 to 60 minutes and the remaining carboxylic acid is then added, also with intensive mixing. In some cases, it may be necessary to heat the reaction mixture to attain the reaction temperature. After another 20 to 60 minutes the reaction is completed. The reaction mixture is cooled, whereupon it separates into organic and aqueous phases. The new procedure can be performed either batchwise or continuously; i.e. in a two-stage stirred cascade. The alpha-alkylacrolein is recovered from the raw product in more than 99% purity by fractional distillation. Additional purification is not necessary for most applications.

The process according to the invention permits the preparation of alpha-alkylacroleins at low temperatures and under conditions which do not require special apparatus. The high yield of unsaturated aldehyde which is obtained despite simple reaction control is remarkable.

The process according to the invention is described in more detail in the following examples. Naturally, it is not intended to limit the invention to the specific embodiments.

EXAMPLES 1 AND 2

In a pressure vessel with a volume of 0.6 m$^3$ equipped with stirrer, the starting aldehyde, formaldehyde (in the form of a 30% aqueous solution), and part of the carboxylic acid in the amounts listed in the table are mixed under a nitrogen atmosphere. All the di-n-butylamine is added within 30 minutes. The reaction mixture is held for another 30 minutes at 95° to 100° C. After the remaining carboxylic acid has been added, the mixture is left to react further for an additional 30 minutes, optionally with stirring. The reaction mixture is cooled, and the aqueous phase separated. The composition of the organic phase is determined by gas chromatography.

TABLE 1

| Preparation of 2-methylacrolein | Example 1 (comparison) | Example 2 |
|---|---|---|
| propionaldehyde (kmol) | 1.8 | 2.16 |
| formaldehyde (kmol) | 1.98 | 2.38 |
| di-n-butylamine (kmol) | 0.045 | 0.054 |
| kmol amine/kmol propionaldehyde | 0.025 | 0.025 |
| propionic acid (kmol) | 0.027 | 0.054 |
| 1st stage | 0.027 | 0.032 |
| 2nd stage | — | 0.022 |
| kmol acid/kmol propionaldehyde | 0.015 | 0.025 |
| kmol acid/kmol amine | 0.6 | 1.0 |
| GC analysis of the organic phase | | |
| 2-methylacrolein (wt. %) | 92.7 | 92.25 |
| aldol (wt. %) | 5.6 | 6.0 |
| after-runnings (wt. %) | 1.5 | |
| yield (% of the theoretical value) | 81.7 | 89.0 |

TABLE 2

| Preparation of 2-ethylacrolein | Example 3 (comparison) | Example 4 (comparison) | Example 5 | Example 6 |
|---|---|---|---|---|
| n-butyraldehyde (kmol) | 1.75 | 2.11 | 1.75 | 1.75 |
| formaldehyde (kmol) | 1.75 | 2.11 | 1.75 | 1.75 |
| di-n-butylamine (kmol) | 0.0446 | 0.0549 | 0.0446 | 0.0446 |
| kmol amine/kmol butyraldehyde | 0.026 | 0.026 | 0.025 | 0.025 |
| n-butyric acid (kmol) | 0.055 | 0.055 | 0.055 | 0.055 |
| 1st stage | 0.055 | 0.055 | 0.018 | 0.0275 |
| 2nd stage | — | — | 0.037 | 0.0275 |
| kmol acid/kmol butyraldehyde | 0.068 | 0.026 | 0.068 | 0.068 |
| kmol acid/kmol amine | 0.3 | 1.0 | 1.0 | 1.0 |
| GC-analysis of org. phase | | | | |
| 2-ethylacrolein (wt. %) | 91.6 | 84.9 | 92.6 | 90.4 |
| Aldol (wt. %) | 3.9 | 5.5 | 1.4 | 0.2 |
| after-runnings (wt. %) | 4.5 | 3.2 | 0.4 | 0.5 |
| yield (% of theor.) | 84.5 | 76.7 | 97.4 | 98.4 |

What we claim is:

1. A process for the preparation of alpha-alkylacrolein comprising a reaction of formaldehyde with a starting aldehyde of the formula

$$RCH_2CH,$$

wherein R is a straight or branched chain alkyl having 1 to 10 carbon atoms, in the presence of, per mol of said starting aldehyde, 0.02 to 0.05 moles of at least one secondary amine selected from the group consisting of dipropylamine, methylbutylamine, ethylbutylamine, di-n-butylamine and di-n-octylamine and;

a total of 0.02 to 0.065 moles of a carboxylic acid having 1 to 5 carbon atoms, at a temperature of 70° to 120° C. and under a pressure of 0.2 to 1.0 MPa, the molar ratio of said amine to said acid being 1:0.8 to 1:1.3, carrying out said reaction in a first step in a mixture of said formaldehyde, said starting aldehyde, said amine, and 25 to 75 mol % of said total of said acid and, as a second stage, adding the rest of said acid to said mixture to complete said reaction.

2. The process of claim 1 wherein there is 0.025 to 0.035 moles of said amine present per mol of said starting aldehyde.

3. The process of claim 1 wherein said total is 0.025 to 0.04 moles.

4. The process of claim 1 wherein said molar ratio is 1:1.1 to 1:1.3.

5. The process of claim 1 wherein said ratio is about 1:1.

6. The process of claim 1 wherein 30 to 65 mol % of said acid is added to said mixture in said first stage.

7. The process of claim 1 wherein said amine is di-n-butylamine.

8. The process of claim 1 wherein said acid is taken from the class consisting of propionic acid, butyric acid, and valeric acid.

9. The process of claim 1 wherein said reaction is carried out at a temperature of 95° C. to 110° C.

10. The process of claim 1 wherein said reaction is carried out under a pressure of 0.2 to 0.4 MPa.

11. The process of claim 1 wherein said starting aldehyde is taken from the class consisting of propanal, n-butanal, 3-methylbutanal, n-pentanal, n-hexanal, 3-methylhexanal, 4-methylhexanal, and n-heptanal.

12. The process of claim 11 wherein said starting aldehyde is taken from the class consisting of propanal, n-butanal, and 3-methylbutanal.

13. The process of claim 1 wherein said formaldehyde is paraformaldehyde.

14. The process of claim 1 wherein there are 0.9 to 1.5 moles of said formaldehyde per mol of said starting aldehyde.

15. The process of claim 1 wherein a solvent is added, and said solvent is taken from the class consisting of hydrocarbons and aliphatic alcohols.

16. The process of claim 15 wherein said solvent is isodecane, toluene, or 2-ethylhexanol.

17. The process of claim 1 wherein said reaction takes place in liquid phase.

18. The process of claim 1 wherein in said first step, said mixture is left to react for 20 to 60 minutes before the commencement of said second stage.

19. The process of claim 18, wherein said mixture is left to react for 20 to 60 minutes after the commencement of said second stage.

* * * * *